Figure 1:
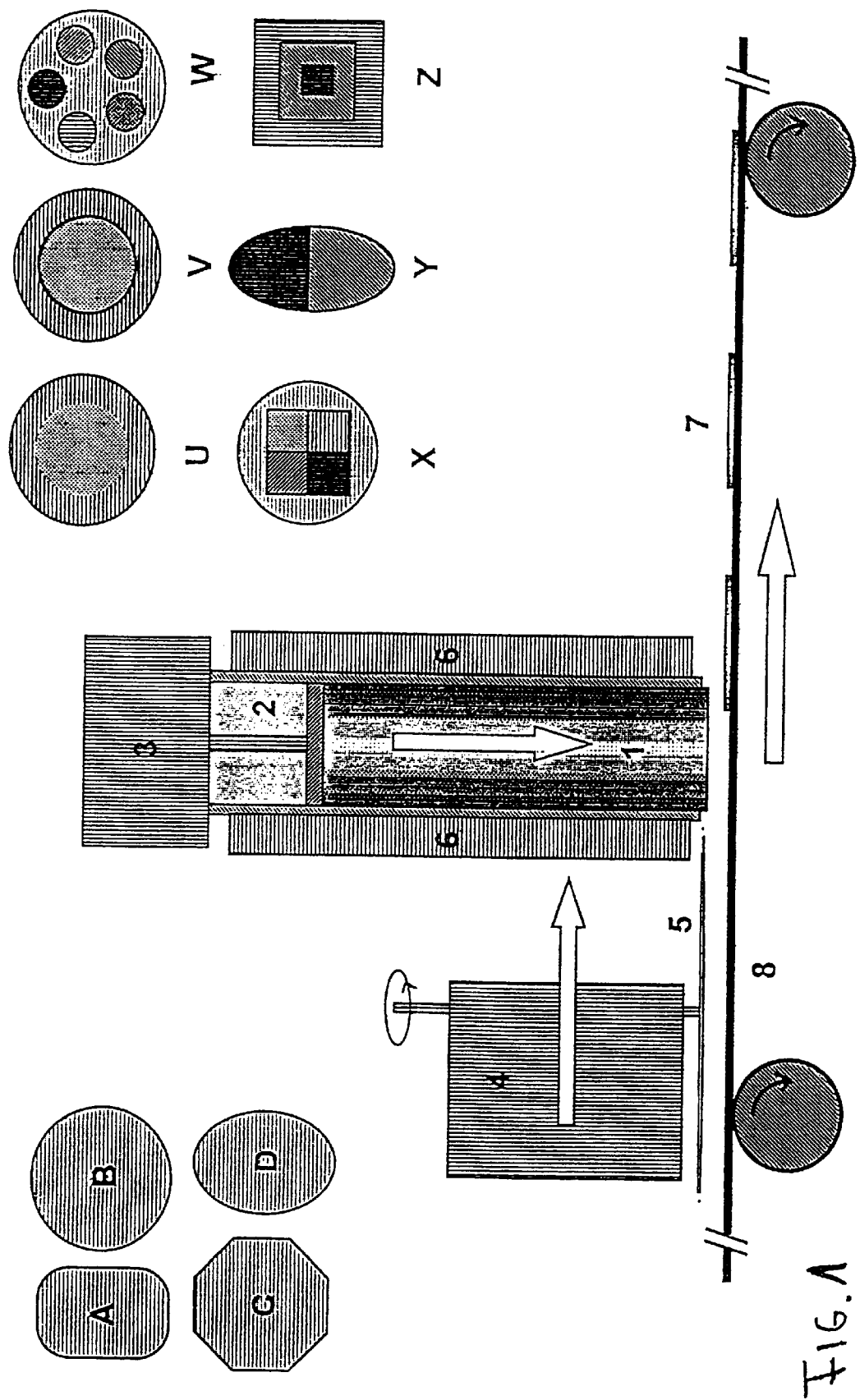

United States Patent
Bracht

[11] Patent Number: 6,156,336
[45] Date of Patent: Dec. 5, 2000

[54] METHOD FOR THE LOW-WASTE MANUFACTURE OF DISKOID MOULDED BODIES CONTAINING ACTIVE INGREDIENTS, AND TRANSDERMAL THERAPEUTIC SYSTEMS CONTAINING SAME

[75] Inventor: Stefan Bracht, Ochtendung, Germany

[73] Assignee: LTS Lohmann Therapie-Systeme GmbH, Neuwied, Germany

[21] Appl. No.: 09/308,428

[22] PCT Filed: Oct. 25, 1997

[86] PCT No.: PCT/EP97/05907

§ 371 Date: Jun. 28, 1999

§ 102(e) Date: Jun. 28, 1999

[87] PCT Pub. No.: WO98/23261

PCT Pub. Date: Jun. 4, 1998

[30] Foreign Application Priority Data

Nov. 27, 1996 [DE] Germany .......................... 196 49 100

[51] Int. Cl.$^7$ ..................................................... A61F 13/00
[52] U.S. Cl. ........................... 424/449; 602/48; 602/900; 424/448
[58] Field of Search .................. 424/449, 474, 424/448, 443; 602/900

[56] References Cited

U.S. PATENT DOCUMENTS 4,666,441  5/1987  Andriola et al. .......................... 604/897
5,464,387  11/1995  Haak et al. ................................ 604/20
5,683,719  11/1997  Newton .................................... 424/474

FOREIGN PATENT DOCUMENTS 35 03 111 A1  1/1985  Germany .
2 249 957  11/1991  United Kingdom .

*Primary Examiner*—Thurman K. Page
*Assistant Examiner*—Isis Ghali
*Attorney, Agent, or Firm*—Law Offices of Jane Massey Licata

[57] ABSTRACT

Active ingredient-containing layered articles or discs which are suitable, in particular, as active ingredient reservoirs for transdermal therapeutic systems are obtained starting from an elongate article having an enveloping surface corresponding to the contour of the layered articles to be produced, and having a cross-sectional constitution corresponding to the internal structure of the layered articles, by layered detachment perpendicular to the axial direction of the elongate article. In the simplest case, this article consists of a uniform active ingredient-containing composition and forms a solid cylinder which is converted into single products perpendicular to the axis with identical spacing to result in circular one-compartment discs identical to one another. The article can, however, have any other external shape and internal structure, in particular be formed by a consolidated bundle of strands with different active ingredients or active ingredient concentrations and be converted into single discs with a plurality of compartments in one plane. Suitable "active ingredients" are not only medicinal substances and their precursors and activators, but also any reagents, auxiliaries, test substances etc.

11 Claims, 1 Drawing Sheet

METHOD FOR THE LOW-WASTE MANUFACTURE OF DISKOID MOULDED BODIES CONTAINING ACTIVE INGREDIENTS, AND TRANSDERMAL THERAPEUTIC SYSTEMS CONTAINING SAME

The invention relates to a process for producing active ingredient-containing layered articles or discs with a uniform or regionally varying constitution within the layer, and to transdermal therapeutic systems having layered articles produced according to the invention.

Active ingredient-containing discs or layered articles can be used in various areas and for various purposes, but a particularly interesting application of such disc-shaped articles is as active ingredient reservoir in transdermal therapeutic systems (TTS). By these are meant active ingredient-containing systems which are placed in contact for a defined time with the surface of the skin or mucous membrane of a human or mammal.

TTS can be made self-adhesive over all or part of the surface, or become self-adhesive under the conditions at the site of application. TTS are used to deliver one or more active ingredients to the contiguous organism in an amount which is determined over time either by the release from the TTS or the absorption capacity of the organism at the site of application. This active ingredient release into the organism can remain locally restricted or else lead to distribution in the whole organism.

In addition, single disc-shaped articles can also be employed in the area of diagnostic aids to be applied dermally, such as, for example, as or for immunological test systems or test series. Systems for transdermal determination of the concentration of particular substances in body fluids, such as, for example, glucose in blood, are also conceivable. In the state of the art, TTS are usually fabricated as sheet-like structures. Such sheet-like structures are produced essentially by punching out the individual pharmaceutical forms from a sheet material which is in web form and onto which previously an active ingredient-containing pharmaceutical preparation—which has generally been made free-flowing by addition of solvent or raising the temperature—has been applied or an active ingredient-containing layered article has been placed.

This punching or cutting out singly is frequently associated with large amounts of waste material, on the one hand from technical necessity, and on the other hand due to the more or less favourable geometry of the individual form.

The typical structure of a TTS furthermore comprises various active or activating components in a multilayer system in the form of an arrangement of individual laminar components stacked one on top of another in only one spatial direction. The individual layers need not have the same shape or area, but may, for example, mutually overlap. This as a rule results in only one or a maximum of two layers being in direct contact with the site of application, whereas all the others are connected indirectly thereto.

The active ingredient can be present in one or more layers of the TTS. The amount of the active ingredient which can be introduced may in some circumstances be limited by the processes customary in the state of the art. Continuous processes with application of layers of solvent-containing active ingredient-containing compositions on to support materials in web form accordingly require a drying, and application of solvent-free compositions in a hot melt process requires corresponding cooling to be allowed.

In batchwise processes, the active ingredient or a suitable preparation thereof is metered intermittently into the substantially prefabricated TTS. The uptake of the active ingredient takes place in this case into suitable cavities or through absorbent carrier materials.

The invention now relates to a process with which it is possible to achieve improvements and extensions of the possibilities for TTS structure and production in three problem areas.

This process consists of a novel way of producing active ingredient-containing layered articles and is essentially characterized in that an elongate article having an inert enveloping surface corresponding to the contour of the layered articles to be produced and having a cross-sectional constitution corresponding to the uniform or regionally varying constitution of the layered articles is converted into single discs perpendicular to the axis.

Further particular aspects of the invention are evident from the claims and the following description.

The process according to the invention offers the following possibilities:

1. It can be used to convert the active ingredient-containing quantity of the starting substances and materials required for TTS production into the finished product with a very high yield. This is desirable in particular with very costly active ingredients, or where waste disposal is associated with strict safety requirements or high costs.
2. The novel process can be used to introduce large amounts of active ingredient easily into a TTS, because the active ingredient-containing composition can be produced and introduced in the form of a semisolid or solid, disc-shaped article. The possible thickness of this article is subject to virtually no technical limitation, in contrast to active ingredient-containing layered articles produced by a coating process. The layered articles produced in the novel way can furthermore be processed in the dimensionally stable state. A distribution or absorption time as with the metering in of liquid active ingredient preparations need therefore not be allowed to elapse or does not represent a limiting factor for the amount which can be metered in.
3. The process according to the invention provides particularly great advantages and extensions of the technical possibilities in the-production of specific multicompartment systems:

A compartment means in this connection a defined space which has a uniform physicochemical constitution and, especially in a TTS, can act as distributing space. A compartment comprises the totality of all the volume elements of a TTS, which are intrinsically homogeneous and have the same structure as one another. In a multilayer TTS according to the state of the art, for example, the individual layers may also represent individual compartments.

It is now possible according to the invention to produce specific multicompartment systems with the aim of accommodating a plurality of compartments side by side carried in one plane of the TTS in order, for example, to bring a plurality of compartments simultaneously into direct contact with the site of application without the need to worry about different active ingredients influencing or interfering with one another, and with the possibility of designing the release or penetration rate individually. On simultaneous delivery of a plurality of active ingredients at one site of application it has hitherto always been necessary to take account of the possibility of incompatibilities of these active ingredients inside only one compartment.

In addition, in very rare cases, the solublility, release and absorption conditions are simultaneously optimal for a plurality of active ingredients inside one and the same compartment. In such cases it is sensible to accommodate the various active ingredients in separate compartments. It is also possible to accommodate one and the same ingredient in different compartments (in different form or concentration) in order, for example, to be able to release an initial dose independently of the maintenance dose.

Advantageous embodiments provide for the cross section of the article to have two or more areas with different active ingredients and/or different active ingredient release rate and/or different active ingredient concentration.

Multicompartment systems also have particular importance in the area of electrophoresis. This involves electrochemical processes being used in order to increase, to expedite or otherwise control in a suitable manner the rate of release of active ingredients from a TTS. The site of application can in this case be part of the electrical circuit. The relevant systems often have a complex internal structure with compartments which are electrochemically separate from one another, but which can now be easily provided in one application plane.

The products of the invention can be employed for producing sheet-like medicinal products, and sheet-like depots for active ingredients of all types which are released to the environment, for example water or atmosphere. The products can furthermore be employed for thin voltaic cells, batteries or accumulators.

By contrast, in the state of the art, it is possible to accommodate simultaneously a plurality of compartments in one plane of a TTS with a layered structure only with difficulty and with restrictions, specific possibilities being, on the one hand, the provision of recesses in one layer which make direct contact with the subsequent layer possible and, on the other hand, mutual overlap of individual layers owing to increasing size. In each case, such a composite of a plurality of layers which vary widely in size and shape can be produced in the state of the art only with difficulty and at high cost.

By contrast, the process according to the invention makes it possible to produce disc-shaped articles which may have a large number of compartments in their area. These compartments are, furthermore, located exactly in a single plane and can therefore, for example, easily be brought into direct contact simultaneously with a flat site of application. Compartments or areas free of active ingredient can be integrated between the individual active ingredient-containing compartments, for example for the purpose of electrochemical isolation or as diffusion barrier. The thickness of the disc-shaped article is advantageously in the range 10–2000 $\mu$m.

The active ingredient-containing layered articles or discs according to the invention are obtained starting from an elongate article with appropriate active ingredient content by detaching discs perpendicular to the long axis.

Active ingredient means in this connection not only bioactive substances such as, in particular, medicinal substances including inactive precursors and activators, but also enhancers, inhibitors, permeation promoters, desiccants, etc. or else test substances or test systems, reagents, etc. The invention has very general uses due to the simple production of optionally active ingredient-containing articles and further processing thereof to a large number of single forms suitable for delivering or receiving substances or groups of substances. These single forms are preferably disc-shaped. They can in the simplest case have a circular to oval outer contour. However, virtually every conceivable contour outline can also be produced. The discs may be completely flat or have recesses.

On production from an elongate article with a constant cross section, by detachment perpendicular or else at a constant inclination to the axis with identical spacing, they may be identical to one another. However, it is also possible straightforwardly, by using elongate articles with a varying cross section and/or by altering the separation spacing and/or the inclination to the long axis, to produce from an elongate article single layered articles which differ from one another.

The detachment takes place by suitable processes such as planing, cutting, sawing, pinching, splitting, etc. The detachment can also take place by high-energy radiation (for example laser radiation) or particle beams. It is moreover possible for the article to be brought to a state, by adjusting the pressure, temperature and/or chemical composition in the surrounding gas space, in which the detachment takes place optimally depending on the separation process chosen. In some circumstances, the article has a solid or semisolid state of aggregation only under the processing conditions, whereas it is transformed into a liquid or from the solid into the semisolid state at room temperature (or, where appropriate, becomes easily separable only under separation conditions). The article preferably has an external geometry and an internal structure and is processed in a spatial direction which makes possible virtually complete conversion into single disc-shaped elements all having the same external geometry and the same internal structure as one another.

In the case of TTS production, the apparatus is ideally adjusted so that the single detached disc-shaped elements reach, by the shortest possible route, a support material which is fed in continuously or batchwise.

Essential for the process according to the invention is the production of the active ingredient-containing article as starting material for the process: this article has in the simplest case the form of a solid cylinder and is divided up into single circular discs in the axial direction perpendicular to the axis. This embodiment is to be understood only as an example; the article can, of course, also have virtually any geometries of the cross sectional area (for example ellipse, polygon or contours which can be described by a Bézier function) on modification of the proportions of a cylinder.

In this case, the longitudinal shape remains characteristic, with the appearance of the cross-sectional area preferably remaining constant along the long axis.

If this article represents only one compartment, it can be produced by casting a suitable composition in a suitable mould and subsequent solidification.

Alternatively, the articles can be produced by pressing a single element in granular form in a suitable mould. Another important process is extrusion, in which the cross-sectional area of the longitudinal product is determined by the shape of the die. It is furthermore possible for an article to be produced by winding an intermediate in web or thread form. In all these processes it is additionally possible to choose specific pressures and temperatures which lead to modifications where appropriate.

Particular interest attaches to the production of elongate articles which afford layered articles with a plurality of compartments:

For this purpose, a plurality of the elongate one-compartment articles produced by one of the above processes can be combined to a joint strand which then forms the starting material for the division up into layered articles. Combination or consolidation of this type can be achieved in a suitable manner by bonding or fusing or baking together the individual articles, by embedding in a casting composition or any other type of combining consolidation of such bundles.

In an extrusion process, it is possible from the outset to combine a number of different compositions emerging simultaneously from a plurality of dies to a joint strand. It is likewise possible to produce an elongate article with a plurality of compartments by casting on use of a suitable multichamber mould. It is furthermore possible for simultaneous, sequential or successive winding of different starting materials in web or thread form to result in a multicompartment strand.

A virtually unlimited number of substances is suitable for producing the elongate articles with one or more compartments, including in particular polymers and polymer-containing preparations. However,-it is also possible for metals such as aluminium, copper, silver, tin, gold and platinum to be present. The substances or mixtures thereof may be sticky in the final product or become sticky on contact with a site of application.

One example of a simple procedure for producing active ingredient-containing layered articles or discs from the articles produced as described above, and useful variants for TTS production are illustrated by means of the appended drawing:

The elongate article 1 is located in a suitable shaft 2 out of which it can be advanced by a precision feed 3. This precision feed operates, for example, via a plunger which is moved by a threaded rod or hydraulically. The accuracy of the metering of active ingredient (disc thickness) depends crucially on the accuracy of this feed apparatus. Single discs are detached from the exposed piece of the article by a unit 4 which is brought up intermittently and on which there is a rotating blade 5. The cutting process is assisted where appropriate by cooling or heating the article with the aid of a jacket 6 (or else the blade 5). The individual discs 7 fall by the shortest route onto support material 8 which is fed in.

The external geometry of the discs 7 depends on the external geometry of the article 1 and can, for example, correspond to the aspect of cross sections A to D. The same applies to the internal structure in multicompartment systems. Some examples thereof are to be found in sketches U to Z. Of these, U and V differ essentially from one another by the two main compartments being separated in the case of V from one another by a thin intermediate compartment which can, for example, form a diffusion barrier or an electrochemical barrier.

What is claimed is:

1. A process for producing active ingredient reservoirs from active-ingredient-containing layered articles or discs with uniform or regionally varying constitution within the layer for use in transdermal therapeutic systems, said process comprising:

(a) die casting or extruding polymers or polymer containing preparations into an elongated article having an active ingredient-containing core and an inert enveloping surface corresponding to a contour of a layered article to be produced and a cross-sectional constitution corresponding to a uniform or regionally varying constitution of the layered article; and (b) converting said elongated article into single discs having a thickness of 10–2000 μm by detaching said discs from said elongated article perpendicularly to a longitudinal axis of said elongated article, wherein detachment is achieved by planing, cutting, sawing, pinching, splitting or by using high-energy radiation or particle beam.

2. The process of claim 1 wherein said elongated article has a uniform cross-sectional area and a uniform cross-sectional constitution of the layered article.

3. The process of claim 1 wherein said elongated article comprises:

bundled strands of different constitution produced by simultaneous extrusion of a number of different polymer compositions and subsequent formation of a joint strand; and a plurality of compartments, so that layered articles and discs with regionally varying constitution are produced.

4. The process of claim 3 wherein the polymer compositions contain different active ingredients.

5. The process of claim 3 wherein the polymer compositions differ in the rate of active ingredient release.

6. The process of claim 3 wherein the polymer compositions differ in active ingredient concentration.

7. The process of claim 3 wherein the polymer compositions comprise different test substances or concentrations thereof for diagnostic purposes.

8. The process of claim 3 wherein the polymer compositions have different electrochemical properties.

9. The process of claim 1 wherein detachment of single discs from said elongated article is achieved by the steps of:

(i) locating the elongated article in an open guide and advancing it in a controlled manner using a precision feed;

(ii) intermittently cutting single discs from the exposed piece of the elongated article by using a rotating blade; and (iii) picking up the single discs by using a support or support belt which is moved past the guide.

10. The process of claim 1 wherein after step (a) of producing said elongated article and prior to step (b) of detaching single discs from the elongated article, the consistency of the elongated article is adjusted to a solid or semi-solid consistency by temperature adjustment.

11. A multi-compartment transdermal therapeutic system having at least one layered article produced according to claim 2 as an active ingredient-containing reservoir, said reservoir having a regionally varying constitution.

* * * * *